United States Patent [19]

Fenici

[11] Patent Number: 5,056,517
[45] Date of Patent: Oct. 15, 1991

[54] BIOMAGNETICALLY LOCALIZABLE MULTIPURPOSE CATHETER AND METHOD FOR MAGNETOCARDIOGRAPHIC GUIDED INTRACARDIAC MAPPING, BIOPSY AND ABLATION OF CARDIAC ARRHYTHMIAS

[75] Inventor: Riccardo Fenici, Rome, Italy

[73] Assignee: Consiglio Nazionale Delle Ricerche, Rome, Italy

[21] Appl. No.: 383,581

[22] Filed: Jul. 24, 1989

[51] Int. Cl.⁵ .............................................. A61N 1/05
[52] U.S. Cl. .................................. 128/419 P; 128/786
[58] Field of Search .................... 128/419 P, 786, 699, 128/784, 785; 606/98, 35

[56] References Cited

U.S. PATENT DOCUMENTS 3,773,037  11/1973  Kolin ..................................... 128/692
4,289,138  9/1981  Halvorsen ......................... 128/419 P
4,630,611  12/1986  King ................................. 128/419 P
4,718,423  1/1988  Willis et al. ..................... 128/419 P Primary Examiner—William E. Kamm
Assistant Examiner—Scott M. Getzow

[57] ABSTRACT

A cardiac electrocatheter with two or more electrodes of non-polarizable and non-ferromagnetic conducting material is described, arranged in such a configuration that an electric field of dipolar configuration can be generated by the two distal electrodes. These two distal electrodes are connected to the other extremity of the catheter by a twisted pair of non-ferromagnetic conductors to prevent spurious magnetic fields generated along the catheter during cardiac pacing. The catheter itself can be made of different kinds of non thrombogenic, flexible, insulated, sterilizable material, with multiple parallel lumens, to allow fluid infusion, suction and/or introduction of ablation or biopsy devices.

11 Claims, 1 Drawing Sheet

BIOMAGNETICALLY LOCALIZABLE MULTIPURPOSE CATHETER AND METHOD FOR MAGNETOCARDIOGRAPHIC GUIDED INTRACARDIAC MAPPING, BIOPSY AND ABLATION OF CARDIAC ARRHYTHMIAS

BACKGROUND OF THE INVENTION

1. Field of the Invention

The subject matter of the present invention consists of a specially designed multilumen electrocatheter which, for its configuration and materials, can be localized and driven close to an arrhythmogenic target in connection with a magnetocardioagraphic mapping and localization technique. The catheter can also be used as a guide for ablation and/or biopsy devices, for fluid infusion and to apply suction.

2. Description of the Prior Art

During the last twenty years, the electrogenetic mechanism of cardiac arrhythmias has been widely investigated the clinical level by combining direct recording of endocardial electrograms and programmable electrical stimulation of the heart.

For both endocardial recording and pacing, commercially available electrocatheters are usually reliable, provided that a recording bandwidth of 30/50–1000 Hz is used. In particular high pass filters are mandatory to obtain stable recordings and avoid offset phenomena due to biological low frequency components (such as respiration) or to polarization of the electrodes during recording and pacing. Filtered signals are reliable for timing local endocardial activation, but inadequate for studying the of transient variation of specific electrophysiological parameters. On the contrary, the recording of monophasic action potential (MAP), a signal which must be typically recorded in open bandwidth (DC to 1 KHz), is gaining a growing interest for the beat-to-beat study of cardiac repolarization and of diastolic arrhythmogenic phenomena under different pathophysiological conditions. At present for MAP recordings, in order to the polarization phenomena, electrocatheters with Ag/AgCl electrodes are used which however polarize if used for pacing. It is evident therefore that it would be impossible to employ the same electrocatheter for monophasic action potential recording and endocardial pacing. On the other hand, MAP recordings have to be carried out in close proximity to the arrhythmogenic areas when diastolic phenomena, such as afterpotentials, have to be identified. A method is needed therefore to drive a mapping catheter, as well as biopsy or ablation devices, right onto the arrhythmogenic zone.

Catheter positioning and localization are usually carried out under fluoroscopic control, with a spatial resolution which is sufficient for routine electrophysiological evaluations, but sometimes inadequate for an accurate three-dimensional localization of arrhythmogenic foci, which is the prerequisite for successful surgical or catheter ablation of arrhythmias. The precision of catheter positioning can be moderately improved by measuring the "local activation time" on the electrograms recorded by the catheter in respect of a fixed reference lead, and taking into account the morphology of the signals.

In order to improve the pre-surgery localization of arrhythmogenic structures, different intracardiac mapping methods have been developed, which imply the use of multielectrode catheters. The spatial localization accuracy of such invasive methods has not been precisely quantified so far. Its average uncertainty is estimated in the order of 1.5–2 cm in the three dimensions.

In patients who undergo open chest surgical ablation of arrhythmias, it is usually possible to verify the preoperative localization accuracy by intraoperative epicardial mapping. On the contrary when catheter ablation is the procedure chosen, the success is only dependent on:

(a) The accuracy of catheter mapping to localize the arrhythmogenic area.

(b) The capability to drive the ablation catheter right within (or as close as possible to) the target arrhythmogenic tissue.

The latter point is obviously more critical when extremely focused ablation energies (i.e. laser, radiofrequency or thermal ablation) are chosen, which determine lesion of only a few millimeters. Catheter positioning reproducibility is extremely important taking into account that in some cases multiple sessions are needed for complete ablation of the arrhythmogenic tissue.

SUMMARY OF THE INVENTION

Within the finalized research project on "Biomagnetism" of the Italian National Research Council, a magnetocardiographic method has been developed, in the Cardiovascular Biomagnetism Unit of the Catholic University of Rome, which allows the non-invasive three-dimensional localization of arrhythmogenic cardiac tissue with a spatial resolution which is at least comparable to that obtainable with the conventional invasive techniques. Moreover, using a prototype of this invented catheter, it has been demonstrated that the tip of the catheter could be three-dimensionally localized within the patient's cardiac volume, by magnetocardiographic mapping performed while pacing the heart with the specially designed distal electrodes.

On the contrary, standard commercially available pacing electrocatheters are not magnetically localizable because of ferromagnetic induced artifacts and/or improper magnetic field pattern generation. On the other hand electrocatheters with Ag/AgCl electrodes are not feasible for cardiac pacing and therefore not localizable by magnetic mapping.

The multipurpose electrocatheter according to the present invention allows:

(1) biomagnetic localization of the tip of the catheter,
(2) monophasic action potential and standard electrograms recording, and
(3) endocardial pacing.

The multipurpose cardiac electrocatheter of the present invention comprises at least two non-ferromagnetic non-polarizable electrodes shaped in such a way as to generate an electric field of dipolar configuration, the two electrodes being connected to the external pacing devices through a pair of copper insulated wires, twisted all along the catheter length up to the electrodes, in order to guarantee absence of magnetic field along the catheter during pacing, the catheter itself being a flexible cylindrical tube of plastic material fully electrically insulated except where the distal and proximal electrodes are placed. The catheter itself is of biocompatible, non-thrombogenic, thin wall plastic material with sufficient torque resistance and pushability.

The cardiac electrocatheter can be provided, besides the lumen for the electrode wires, with other multiple parallel lumens, with terminal and/or lateral eyelets, to insert ablation wires or fiberoptics, to apply suction, intracardiac pressure measurements and fluid infusion.

In a specific embodiment of the present invention the distal electrode can be hemispherically shaped and the proximal electrode can be ring-shaped.

In another embodiment both the distal and proximal electrodes can be ring-shaped.

The equivalent surface of the electrodes in the cardiac electrocatheter of the invention ranges between 5 and 15 mm$^2$.

The interelectrode distance ranges between 2 and 7 mm.

The material used for the electrodes is preferably selected from the group comprising platinated platinum and amorphous carbon.

The internal wires are insulated pure copper twisted pairs (diameter about 200 $\mu$m). Such a material should be appropriately worked to be flexible and torque resistant.

The catheter tube material is preferabaly selected from the group comprising polyurethan, polyethylenterephtalate, polyethylene or polyvinylchloride.

The size of the catheter can range between 1.67 and 2.60 mm (5 and 8 F, F meaning French).

The catheter according to the present invention can be used for:

(A) Conventional (filtered) intracardiac mapping;

(B) Intracardiac mapping of monophasic action potentials.

(C) Calibration of biomagnetic systems for accuracy of cardiac sources localization;

(D) Biomagnetic localization of the catheter tip position with respect to the site of origin of cardiac arrhythmias, previously localized by magnetocardiographic mapping; and (E) An integrated system for biomagnetically driven intracardiac catheter ablation of arrhythmogenic tissue and/or endomyocardial biopsy.

After the general description of this multipurpose catheter, a more detailed explanation is now given of possible variants for special applications in connection with biomagnetic imaging.

DESCRIPTION OF THE PREFERRED EMBODIMENT

Figure 1:
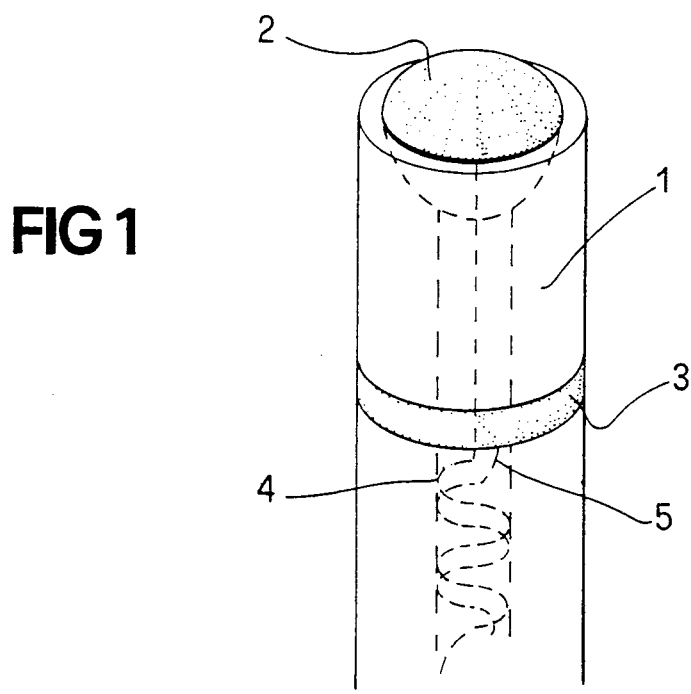
FIG. 1 shows a perspective view of the catheter tip (dashed lines indicate the internal parts) in the simplest configuration.

In FIG. 1, the catheter wall in polyurethan is indicated by 1. The distal (tip) hemispheric electrode 2, and the proximal (ring) electrode 3 are both made of platinated platinum. 4 and 5 are the internal copper wires (diameter: 200 $\mu$m) distally connected to the distal electrode 2 and to the proximal electrode 3 respectively. The electrodes' equivalent surface is 7 square millimeters. The interelectrode distance is 5 mm. The external catheter size is 5 F (1.67 mm).

Figure 2:
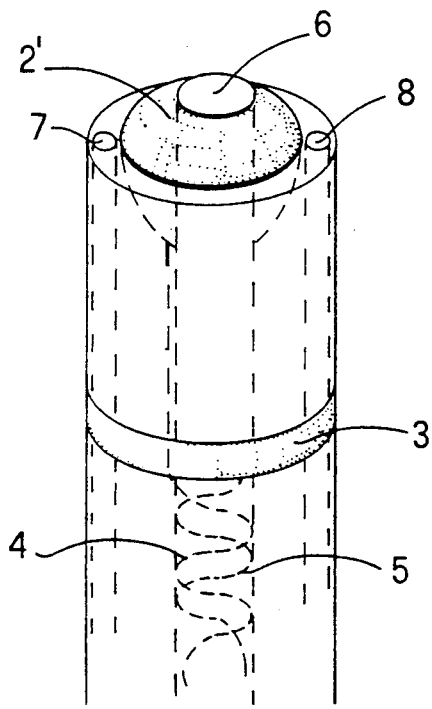
FIG. 2 shows a perspective view of the catheter tip in the multilumen configuration which features one central and two parallel lateral lumens (eyelets can be lateral and/or at the tip of the catheter)
Figure 3:
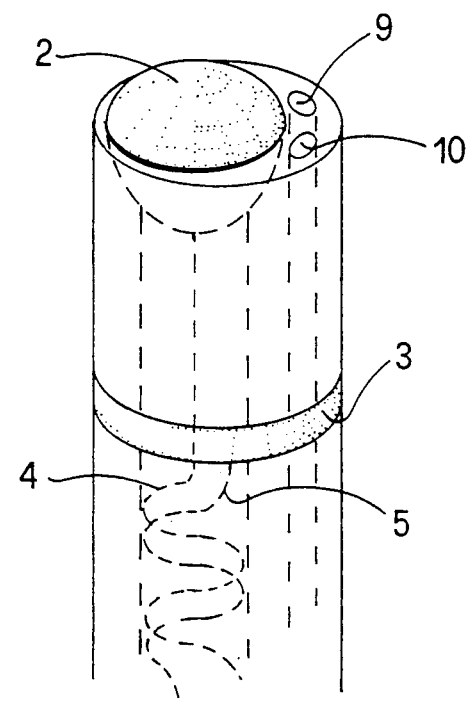
FIG. 3 shows a perspective view of the catheter tip in a configuration which features only two parallel lumens, with tip or lateral eyelets.

In FIG. 2, a different configuration of the catheter is shown which features a central lumen 6 (diameter=0.035 inches, i.e. 0.889 mm) and two thinner lateral lumens 7 and 8, available to introduce fiberoptics or ablation wires, apply suction or fluid infusion. The central lumen implies the anular configuration of the distal electrode 2, while the proximal electrode 3 is unchanged. In FIG. 3, a third catheter configuration is shown, which features only two lateral lumens 9 and 10, available for ablation wires and/or fiberoptics introduction.

The biomagnetic driving technique of the ablation catheter on the arrhythmogenic target comprises the following steps:

one or more preliminary magnetocardiographic studies of the patient are performed to identify the reproducibility of the magnetic field distribution generated by the arrhythmogenic structures to be ablated, the three-dimensional localization of the arrhythmogenic area being obtained by inverse solution with the equivalent current dipole or current multipole expansion models;

on the basis of this and other conventional localization procedures the biomagnetically drivable ablation catheter is placed, under fluoroscopic control, as close as possible to the target zone;

a magnetocardiographic mapping is performed during cardiac pacing through the catheter artificial dipole (electrodes 2 and 3); and the catheter position is reliable for ablation when the paced field fits at the best the magnetic field distribution generated by the arrhythmogenic structure, or accepted as representative of the site of origin of the arrhythmia to be treated.

I claim:

1. A multipurpose cardiac electrocatheter for use with an external pacing device, comprising:

at least two non-ferromagnetic non-polarizable electrode means for generating an electric field having a dipolar configuration;

a pair of copper insulated wires connected to said electrode means;

said pair of copper insulated wires being twisted along a total length of the multipurpose cardiac electrocatheter up to said electrodes;

said electrode means forming a distal electrode and a proximal electrode;

said pair of copper insulated wires preventing generation of spurious magnetic fields along the multipurpose cardiac electrocatheter during pacing operations; and a flexible cylindrical tube constructed of plastic electrically insulated material.

2. The multipurpose cardiac electrocatheter as claimed in claim 1, further comprising:

a lumen for said copper insulated wires; and multiple parallel lumens with terminals or lateral eyelets for inserting ablation wires or fiberoptics to apply suction or fluid infusion.

3. The multipurpose cardiac electrocatheter as claimed in claims 1 or 2, wherein said distal electrode is hemispherically shaped and said proximal electrode is ring-shaped.

4. The multipurpose cardiac electrocatheter as claimed in claims 1 or 2, wherein said distal and proximal electrodes are ring shaped.

5. The multipurpose cardiac electrocatheter as claimed in claim 1, wherein a surface area of said electrodes ranges between 5 and 15 mm$^2$.

6. The multipurpose cardiac electrocatheter as claimed in claim 1, wherein an interelectrode distance ranges between 2 and 7 mm.

7. The multipurpose cardiac electrocatheter as claimed in claim 1, wherein said electrode means are constructed of material selected from a group comprising platinated platinum and amorphous carbon.

8. The multipurpose cardiac electrocatheter as claimed in claim 1, wherein said copper insulated wires are made of pure copper, said copper insulated wires being about 200 microns in diameter.

9. The multipurpose cardiac electrocatheter as claimed in claim 1, wherein said flexible cylindrical tube is made from material selected from a group comprising polyurethane, polyethylenterephtalate, polyethylene and polyvinylchloride.

10. The multipurpose cardiac electrocatheter as claimed in claim 1, wherein the multipurpose cardiac electrocatheter is between 1.67 and 2.60 mm in diameter.

11. A method for biomagnetically driving a multipurpose catheter in proximity of an arrhythmogenic area to improve diagnostic and localization accuracy of intracardiac mapping and biopsy and to increase effectiveness of endomyocardial ablation of cardiac arrhythmias, comprising the steps of:
(a) preforming one or more preliminary magnetocardiographic studies on a patient to identify reproducibility of a magnetic field distribution generated by arrhythmogenic structures to be ablated;
(b) obtaining a three-dimentional localization of the arrhythmogenic area by inverse solution with equivalent current dipole or current multiple expansion models;
(c) fluoroscopically controlling the biomagnetically drivable ablation catheter as close as possible to a target zone;
(d) magnetocardiographically mapping during cardiac pacing using an artificial dipole generated by the multipurpose catheter; and
(e) fitting a paced field with a magnetic field distribution generated by the arrhythmogenic structure to position the multipurpose cardiac electrocatheter for ablation.

* * * * *